United States Patent [19]
Riso

[11] Patent Number: 5,775,901
[45] Date of Patent: Jul. 7, 1998

[54] INSERT FOR ULTRASONIC SCALER

[75] Inventor: Anthony T. Riso, Bal Harbor, Fla.

[73] Assignee: Hu-Friedy Mfg. Co., Ltd., Chicago, Ill.

[21] Appl. No.: 612,516

[22] Filed: Mar. 7, 1996

[51] Int. Cl.$^6$ .................................................. A61C 1/07
[52] U.S. Cl. .................................. 433/86; 432/119
[58] Field of Search ................................. 433/86, 119

[56] References Cited

U.S. PATENT DOCUMENTS

| | | | |
|---|---|---|---|
| Re. 30,536 | 3/1981 | Perdreaux, Jr. | 433/86 |
| 2,442,033 | 5/1948 | Brantly et al. | 32/28 |
| 2,705,838 | 4/1955 | Blair | 32/28 |
| 3,058,218 | 10/1962 | Kleesattel et al. | 32/27 |
| 3,075,288 | 1/1963 | Balamuth et al. | 32/58 |
| 3,076,904 | 2/1963 | Kleesattel et al. | 310/26 |
| 3,124,878 | 3/1964 | Bodine, Jr. et al. | 433/119 |
| 3,213,537 | 10/1965 | Balamuth et al. | 32/58 |
| 3,256,604 | 6/1966 | Borden | 32/28 |
| 3,368,280 | 2/1968 | Friedman et al. | 32/58 |
| 3,375,583 | 4/1968 | Blank et al. | 32/26 |
| 3,488,851 | 1/1970 | Haydu | 32/58 |
| 3,518,766 | 7/1970 | Burt | 32/58 |
| 3,522,801 | 8/1970 | Robinson | 128/66 |
| 3,526,036 | 9/1970 | Goof | 32/28 |
| 3,589,012 | 6/1971 | Richman | 32/58 |
| 3,589,363 | 6/1971 | Banko et al. | 128/276 |
| 3,593,425 | 7/1971 | Robinson | 32/58 |
| 3,636,947 | 1/1972 | Balamuth | 128/66 |
| 3,645,255 | 2/1972 | Robinson | 128/24 A |
| 3,654,502 | 4/1972 | Carmona et al. | 310/26 |
| 3,654,540 | 4/1972 | Honig et al. | 318/118 |
| 3,703,037 | 11/1972 | Robinson | 32/58 |
| 3,809,977 | 5/1974 | Balamuth et al. | 318/116 |
| 3,874,470 | 4/1975 | Richards | 32/58 |
| 3,882,638 | 5/1975 | Black | 51/12 |
| 3,930,173 | 12/1975 | Banko | 310/26 |
| 3,956,826 | 5/1976 | Perdreaux, Jr. | 32/58 |
| 3,972,123 | 8/1976 | Black | 32/58 |
| 4,110,908 | 9/1978 | Cranston | 32/50 |
| 4,370,131 | 1/1983 | Banko | 433/86 |
| 4,492,574 | 1/1985 | Warrin et al. | 433/81 |
| 4,820,152 | 4/1989 | Warrin et al. | 433/86 |
| 5,382,162 | 1/1995 | Sharp | 433/116 |

Primary Examiner—Nicholas D. Lucchesi
Attorney, Agent, or Firm—Rockey, Milnamow & Katz, Ltd.

[57] ABSTRACT

An insert for an ultrasonic scaling instrument includes an elongated body. A plastic gripping collar surrounds the insert near one of the ends. A fluid input port is on an end of the collar. An internal conduit extends between the fluid flow input port through the plastic collar to a fluid flow output channel. A metal fluid flow output conduit is rigidly clamped by the collar into a portion of the fluid flow output channel. An output end of the conduit is directed toward an adjacent scaling tip carried by the insert. The fluid from the conduit is directed onto a portion of the scaling tip. Depending on fluid flow pressure, part of the fluid can be directly scattered thereby, and part of the fluid can flow along the tip to an end thereof and then be scattered at the end. The collar provides a rigid coupling between the conduit and the body portion so that vibrations of the body portion do not alter the relative position of the output conduit relative to the tip.

23 Claims, 2 Drawing Sheets

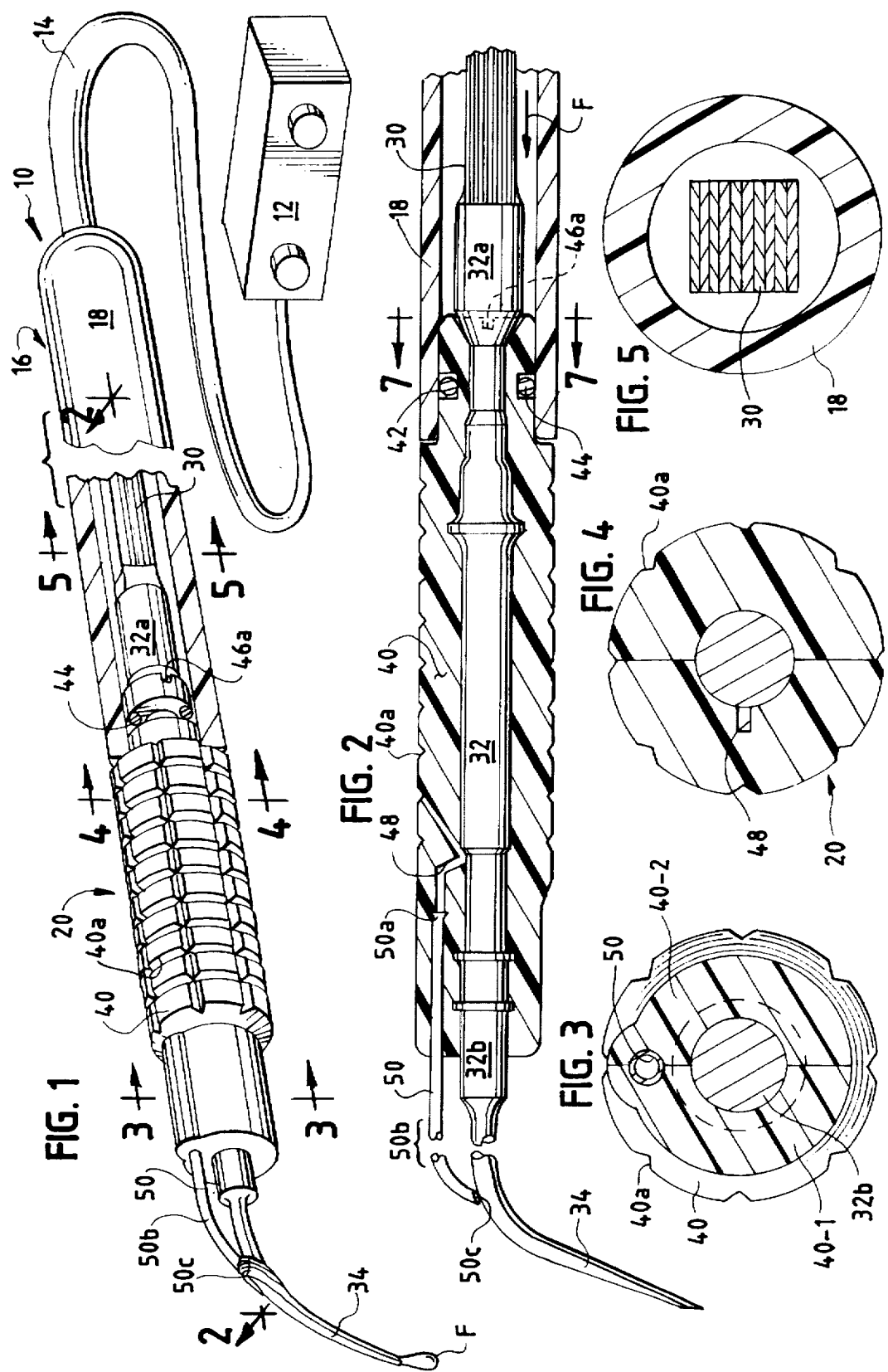

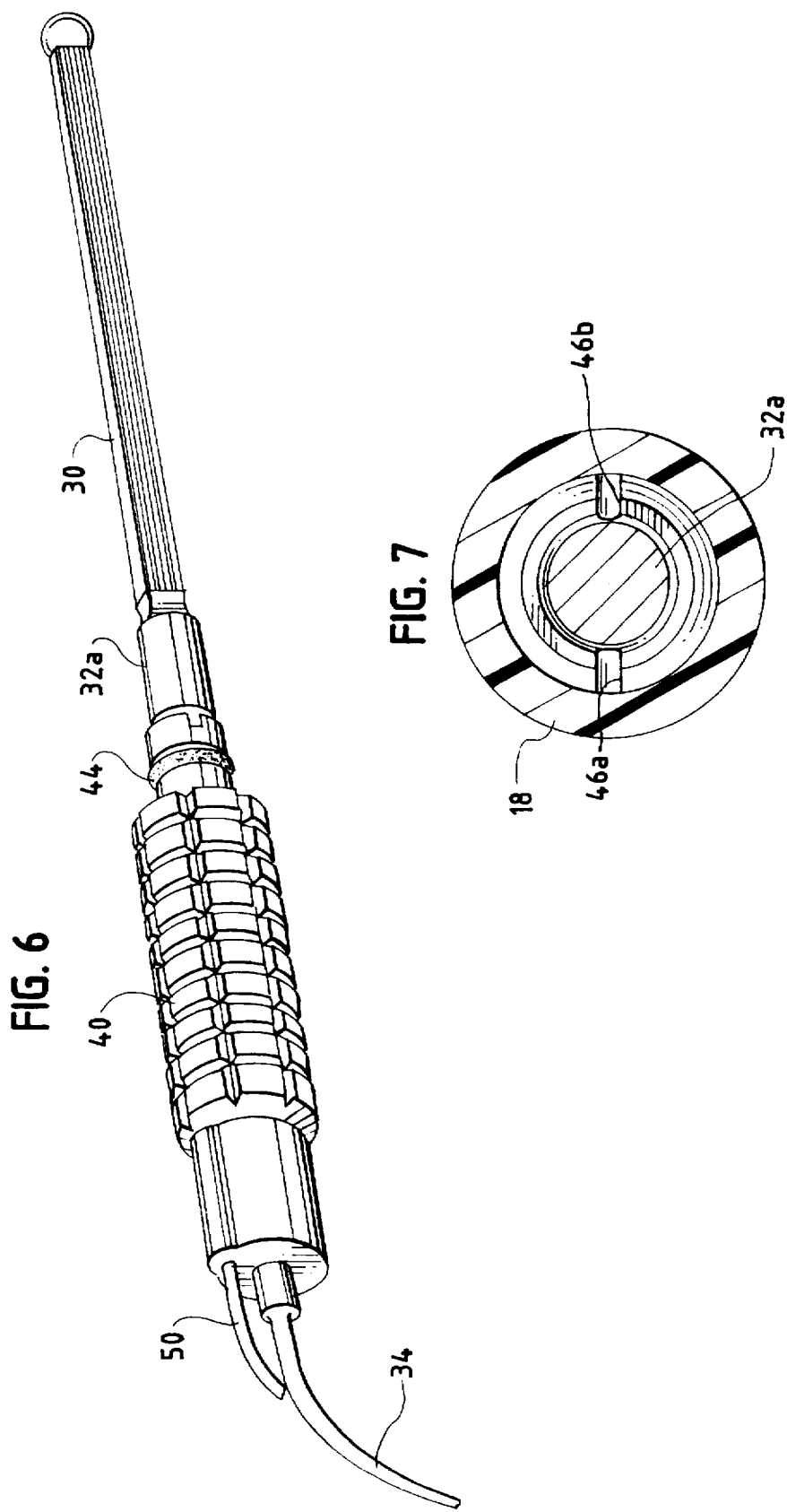

INSERT FOR ULTRASONIC SCALER

FIELD OF THE INVENTION

The invention pertains to ultrasonic scaling instruments. More particularly, the invention pertains to replaceable inserts for such instruments.

BACKGROUND OF THE INVENTION

Ultrasonic dental cleaning and scaling instruments have long been recognized as useful in promoting oral hygiene. Such instruments are disclosed in U.S. Pat. No. 3,636,947 entitled "ULTRASONIC HOME DENTAL INSTRUMENT AND METHOD."

Known ultrasonic scaling instruments usually include replaceable inserts which respond to a 25 KHz or 30 KHz driving signal which originates at a remote control unit. These signals along with a flushing fluid, often water, are coupled to a hollow hand piece. The insert is carried in the hand piece.

The high frequency signals impart an axial vibration to the insert. This in turn causes a distal treatment applying tip of the insert to vibrate at a high frequency.

A stream of fluid is ejected under pressure from an output port near the distal end. The fluid is directed toward the treatment applying tip and can be disbursed thereby onto adjacent tooth surfaces or tissue.

Known fluid delivery arrangements suffer from several drawbacks. Sometimes the fluid delivery conduit changes position due to the vibrations. Other delivery arrangements do not direct the fluid flow optimally. Some of the fluid delivery arrangements increase manufacturing cost and/or complexity.

There thus continues to be a need for more rigid fluid delivery arrangements where the fluid is optimally directed to the treatment imparting distal tip of the insert. Preferably these needs could be met without significantly increasing manufacturing costs for the inserts.

SUMMARY OF THE INVENTION

An ultrasonic insert has a proximal end and a distal end. Spaced from the proximal end, toward the distal end, is a fluid flow input port. An internal flow path, extends toward the distal end. The distal end of the insert carries a scaling probe or tip.

A fluid flow output tube is fixedly attached to the insert and extends along and is spaced apart from the distal end. The tube is tightly clamped to the insert so as to eliminate movement thereof. Fluid is ejected under pressure from an output port of the output tube and is intended to be disbursed along a treatment providing portion of the or tip.

In a preferred embodiment, the flow tube is spaced from the distal end and extends, in part, parallel thereto. The fluid output end of the flow tube has a curvature to direct the fluid optimally toward the tip.

Numerous other advantages and features of the present invention will become readily apparent from the following detailed description of the invention and the embodiments thereof, from the claims and from the accompanying drawings.

BRIEF DESCRIPTION OF THE DRAWINGS

FIG. 1 is an enlarged perspective view of an ultrasonic scaling system which incorporates an ultrasonic insert in accordance with the present invention;

FIG. 2 is a side-sectional view of a portion of the system of FIG. 1 taken along plane 2—2 thereof;

FIG. 3 is an axial sectional view of the insert of FIG. 1 taken along plane 3—3 thereof;

FIG. 4 is an axial sectional view of the insert of FIG. 1 taken along plane 4—4 thereof;

FIG. 5 is an axial sectional view of a portion of the system of FIG. 1 taken along plane 5—5 thereof;

FIG. 6 is a perspective view of the insert; and

FIG. 7 is an axial sectional view of the insert of FIG. 2 taken along plane 7—7.

DETAILED DESCRIPTION OF THE DRAWINGS

While this invention is susceptible of embodiment in many different forms, there are shown in the drawing and will be described herein in detail specific embodiments thereof with the understanding that the present disclosure is to be considered as an exemplification of the principles of the invention and is not intended to limit the invention to the specific embodiments illustrated.

FIG. 1 illustrates an ultrasonic scaling system 10. The system 10 includes a control unit 12 of a conventional type for providing high frequency electrical signals, in a range of 20 to 40 KHz. A cable 14 includes conductors for the electrical signals generated by the unit 12 as well as a flow path to provide water or some form of fluid antibiotic to be applied to the teeth and gums of an individual being treated.

The cable 14 couples the control unit 12 to a hand-held unit generally indicated at 16. The unit 16 includes an exterior, hollow, outer sheath 18. The sheath 18 could be formed as a cylindrical hollow plastic member. A variety of plastics are useable and those would be known to individuals of skill in the art.

Coupled to the sheath 18, is an ultrasonic scaling insert generally indicated at 20. The insert 20 removably engages the sheath 18 by means of a conventional locking mechanism also of a type known to those of skill in the art.

The insert 20 is removable from the sheath 18 for purposes of autoclaving between uses. It will be understood that a variety of different inserts could be used with a sheath 18 without departing from the spirit and scope of the present invention.

The insert 20 includes a stack of laminar plates of magnetostrictive material 30 such as a nickel alloy which is excited by a coil (not illustrated) in the sheath 18 as is conventional. The coil is energized by electrical signals transmitted by cable 14 from the source 12.

The stack of plates 30 longitudedly expands and contracts at the ultrasonic frequency of the signals supplied from the unit 12. As is well known, this expansion and contraction imparts a vibratory motion to the insert 20.

The insert 20 includes a stainless steel body portion 32 which is brazed to the stack of plates 30. The body portion 32 has a proximal extension end 32a adjacent to the plates 30 and a distal end 32b. The distal end 32b carries a solid scaling probe or tip 34 of stainless steel.

The tip or probe 34 can assume a variety of different sizes and shapes depending on the exact type of dental treatment to be provided. It will be understood that these variations in the probe 34 come within the spirit and scope of the present invention.

The insert 20 carries an elongated, molded plastic grip or collar 40 having gripping elements or depressions 40a. The elements or depressions 40a provide a non-slip gripping surface for the insert 20. The collar 20 could be formed by a polyetherimide resin.

The collar 40 surrounds the body 32 of the insert 20 and extends between the proximal end 32a and the distal end 32b.

The collar includes an annular ring 42 adjacent to the proximal end 32a wherein 0-ring 44 is positioned. The 0-ring 44 functions as a fluid seal and prevents leakage of fluid F which is forced under pressure into the sheath 18 via cable 14. A second O-ring seal is located in the collar 40 adjacent to the distal end 32b.

The fluid F enters the collar 40 at fluid flow input ports 46a and 46b and travels through an internal flow path 48 in the collar 40 toward the distal end 32b. The flow path 48 terminates in an output flow tube 50 which is rigidly carried by the collar 40.

The tubular member 50 provides an output path for the pressurized fluid F. The tubular member 50 has a first end 50a which is in fluid flow communication with the flow path 48 within the collar 40.

The end 50a is flared slightly to provide for better contact with and gripping by the collar 40. The output tubular member 50 has a curved region 50b which terminates at a fluid flow output port 50c. The output port 50c has a predetermined orientation with respect to the probe 34.

As is illustrated in FIG. 2, the flow tube 50, which could be, for example a stainless steal tubular member, extends in part parallel to the body portion 32 and then curves toward the probe 34. The collar 40 maintains both the probe 34 and the output port 50c of the tubular member 50 in a substantially fixed relationship with one another notwithstanding the vibrations exhibited by the probe 34 when in use. This rigid connection between the probe 34 and the output flow conduit 50 keeps the output port 50c in a fixed optimal orientation with respect to the probe 34.

FIG. 3 illustrates a sectional view of the insert 20 in a region adjacent to the distal end 32b. FIG. 4 illustrates a sectional view of the insert 20 in a region between the proximal end 32a and the distal end 32b.

As illustrated in FIGS. 3 and 4, the collar 40 can be formed of first and second parts 40-1 and 40-2. The two parts 40-1 and 40-2 can then be assembled with the body portion 32 and the output conduit 50 and ultrasonically welded together to form a single mechanically stable unit.

FIG. 5 illustrates a section of the sheath 18 with the laminated stack 30 positioned therein. FIG. 6 is a view of the insert apart from the sheath. FIG. 7 is a sectional view illustrating the fluid flow input ports.

From the foregoing, it will be observed that numerous variations and modifications may be effected without departing from the spirit and scope of the invention. It is to be understood that no limitation with respect to the specific apparatus illustrated herein in tended or should be inferred. It is, of course, intended to cover by the appended claims all such modifications as fall within the scope of the claims.

I claim:

1. An insert for an ultrasonic scaler comprising:
   an elongated body, having first and second ends;
   an elongated scaling probe having first and second ends wherein one of said probe ends is connected to one of said ends of said body;
   a molded, elongated collar with first and second ends, wherein one end of said collar surrounds a portion of said one end of said body thereby forming a substantially rigid, unified structure and wherein a fluid flow input port is defined by said collar at said other end thereof and wherein an internal flow path is defined between said input port and said one end of said collar; and
   a fluid flow conduit having first and second ends wherein said conduit is arranged with one of said ends in fluid flow communication with said internal flow path and wherein said collar rigidly surrounds said one end of said conduit with said other end thereof extending from said collar, displaced from said first probe end, and oriented to direct a fluid flow onto a portion of said probe wherein said one end of said conduit is fixedly retained by said collar thereby preventing relative movement between said conduit and said probe.

2. An insert as in claim 1 wherein said collar carries an external, non-slip, gripping surface.

3. An insert as in claim 1 wherein said collar includes a molded extension surrounding, at least in part, said conduit.

4. An insert as in claim 1 wherein said collar is formed of first and second portions which are welded together.

5. An insert for an ultrasonic dental instrument, comprising:
   an elongated body, being a substantially cylindrical rod with at least one radially extending portion and having a body base end couplable to a source of ultrasonic energy and a body distal end;
   an elongated probe having a probe distal end and a probe base end wherein said probe base end is connected to said body distal end;
   a molded, elongated collar having a collar base end and a collar distal end, wherein said collar surrounds said elongated body, and said elongated collar having a longitudinal recess forming an internal flow path, open to a fluid flow input port defined by said collar at said collar base end; and
   a fluid flow conduit having a conduit base end and a conduit distal end, wherein said conduit is arranged with said conduit base end in fluid flow communication with said internal flow path, said collar rigidly surrounding a first portion of said conduit adjacent to said conduit base end, and a second portion of said conduit extending outwardly from said collar distal end to said conduit distal end, said conduit distal end displaced from said probe distal end and oriented to direct a fluid flow onto a portion of said probe wherein said conduit is fixedly retained by said collar thereby preventing relative movement between said conduit and said probe.

6. An insert as in claim 5 wherein said collar carries an external, non-slip gripping surface.

7. An insert as in claim 5 wherein said collar includes a molded extension surrounding, at least in part, said conduit.

8. An insert as in claim 5 wherein said collar is formed of first and second portions which are welded together.

9. An insert as in claim 5 wherein said collar is substantially cylindrical, having two diametrically opposed seams along the length thereof.

10. An insert as in claim 5 wherein said recess is a groove arranged adjacent to said body.

11. An insert as in claim 5 wherein said probe and said second portion of said conduit extend from said collar distal end and bend in a substantially common plane to each extend at an angle to a longitudinal direction of said elongated body.

12. An insert as in claim 11 wherein said second portion of said conduit is bent toward said probe base end.

13. An insert as in claim 5 wherein said conduit distal end is displaced from said probe.

14. An insert as in claim 5 wherein said first portion of said conduit has a length approximately equal to a length of said second portion of said conduit.

15. An insert as in claim 5 wherein said second portion of said conduit is spaced from said probe.

16. An insert as in claim 5 wherein said collar has an end opening at the collar base end for said elongated body to protrude outwardly therefrom at said body base end; and further comprising a stack of laminar plates of magnetostrictive material connected to and extending axially from said elongated body at said body base end, said stack extending outside of said collar.

17. An insert as in claim 16 wherein said collar carries an external, nonslip gripping surface.

18. An insert as in claim 16 wherein said collar includes a molded extension surrounding, at least in part, said conduit.

19. An insert as in claim 16 wherein said collar is substantially cylindrical and said collar base end has a reduced diameter forming a step, and said collar base end includes a seal around its circumference for insertion into an ultrasonic tool.

20. An ultrasonic insert usable with a dental tool having an elongated, cylindrical body which defines an internal insert receiving region and an insert receiving end, wherein the insert extends into and slidably engages the body, wherein the insert when so inserted extends in part from the end of the body, the insert comprising:

manually manipulatable cylindrical, molded handle which has a distal end from which extends a metal fluid flow conduit, in part surrounded by a first portion of the molded handle and an operative ultrasonic probe, spaced from the flow conduit, wherein the probe is in part surrounded by a second portion of the molded handle, laterally displaced from the first portion with a third portion of the handle extending therebetween whereby the portions of the handle substantially determine the positions of the conduit and the probe relative to one another.

21. An insert as in claim 20 wherein the conduit is coupled to an internal flow path molded into the handle portion.

22. An insert as in claim 20 wherein the handle carries a resiliant seal for removably engaging a portion of the handle.

23. An insert as in claim 20 wherein the probe is formed with a closed distal end.

* * * * *